United States Patent [19]

Hori et al.

[11] Patent Number: 5,603,687
[45] Date of Patent: Feb. 18, 1997

[54] ASYMMETRIC STEREO-OPTIC ENDOSCOPE

[75] Inventors: Koichiro Hori, Framingham, Mass.; John R. Lyon, Escondido, Calif.

[73] Assignee: Oktas General Partnership, Westborough, Mass.

[21] Appl. No.: 475,364

[22] Filed: Jun. 7, 1995

Related U.S. Application Data

[63] Continuation-in-part of Ser. No. 400,503, Mar. 7, 1995, which is a continuation of Ser. No. 967,996, Oct. 28, 1992, abandoned.

[51] Int. Cl.⁶ ..................................................... A61B 1/04
[52] U.S. Cl. ...................... 600/166; 600/111; 600/130; 600/176; 348/45
[58] Field of Search ..................................... 600/101, 111, 600/166, 130, 176; 359/376, 462, 464, 466; 348/45, 42, 47

[56] References Cited

U.S. PATENT DOCUMENTS

| | | |
|---|---|---|
| 3,520,587 | 7/1970 | Tasaki et al. . |
| 3,534,729 | 10/1970 | Sakamoto . |
| 3,655,259 | 4/1972 | Miyauchi et al. . |
| 4,615,332 | 10/1986 | Buess et al. . |
| 4,651,201 | 3/1987 | Schoolman . |
| 4,834,518 | 5/1989 | Barber . |
| 4,862,873 | 9/1989 | Yajima et al. . |
| 4,873,572 | 10/1989 | Miyazaki . |
| 4,924,853 | 5/1990 | Jones, Jr. . |
| 4,926,257 | 5/1990 | Miyazaki . |
| 5,109,276 | 4/1992 | Nudelman et al. . |
| 5,122,650 | 6/1992 | McKinley . |
| 5,191,203 | 3/1993 | McKinley . |
| 5,200,819 | 4/1993 | Nudelman et al. . |
| 5,200,838 | 4/1993 | Nudelman et al. . |
| 5,222,482 | 6/1993 | Clark . |
| 5,261,404 | 11/1993 | Mick et al. . |
| 5,305,121 | 4/1994 | Moll . |

FOREIGN PATENT DOCUMENTS

| | | |
|---|---|---|
| 0211783 | 2/1987 | European Pat. Off. . |

OTHER PUBLICATIONS

Kooi, F. L.; "Binocular Configurations of a Night–Flight Head–Mounted Display"; Displays, vol. 14, No. 1; 1993; pp. 11–20.

Wood, Robert and Cochran, Will; "Stereoendoscopy Gives Surgeons Normal Vision"; Photonics Spectra; Sep. 1993; p. 40.

Schor, Clifton; Landsman, Lori; Erickson, Paul; "Ocular Dominance and the Interocular Suppression of Blur in Monovision"; Am. J. of Optometry & Physiological Optics, vol. 64, No. 10; 1987; pp. 723–730.

Primary Examiner—Richard J. Apley
Assistant Examiner—John P. Leubecker
Attorney, Agent, or Firm—Pandiscio & Pandiscio

[57] ABSTRACT

An endoscope for stereo-optically viewing an object comprises a tubular insertion portion characterized by a pair of adjacent asymmetric optical systems including a primary imaging channel and a secondary imaging channel. Associated with each channel is a solid state electronic imaging means positioned to receive the images relayed by primary and secondary image-relaying means. The optical portion of the primary channel comprises a relatively large objective lens system and a primary image-relaying means designed to provide sharply focussed first images. The optical portion of the secondary channel comprises a relatively small diameter objective lens system and a secondary image-relaying means designed to relay enough light and image information to provide an acceptable stereoscopic capability.

40 Claims, 4 Drawing Sheets

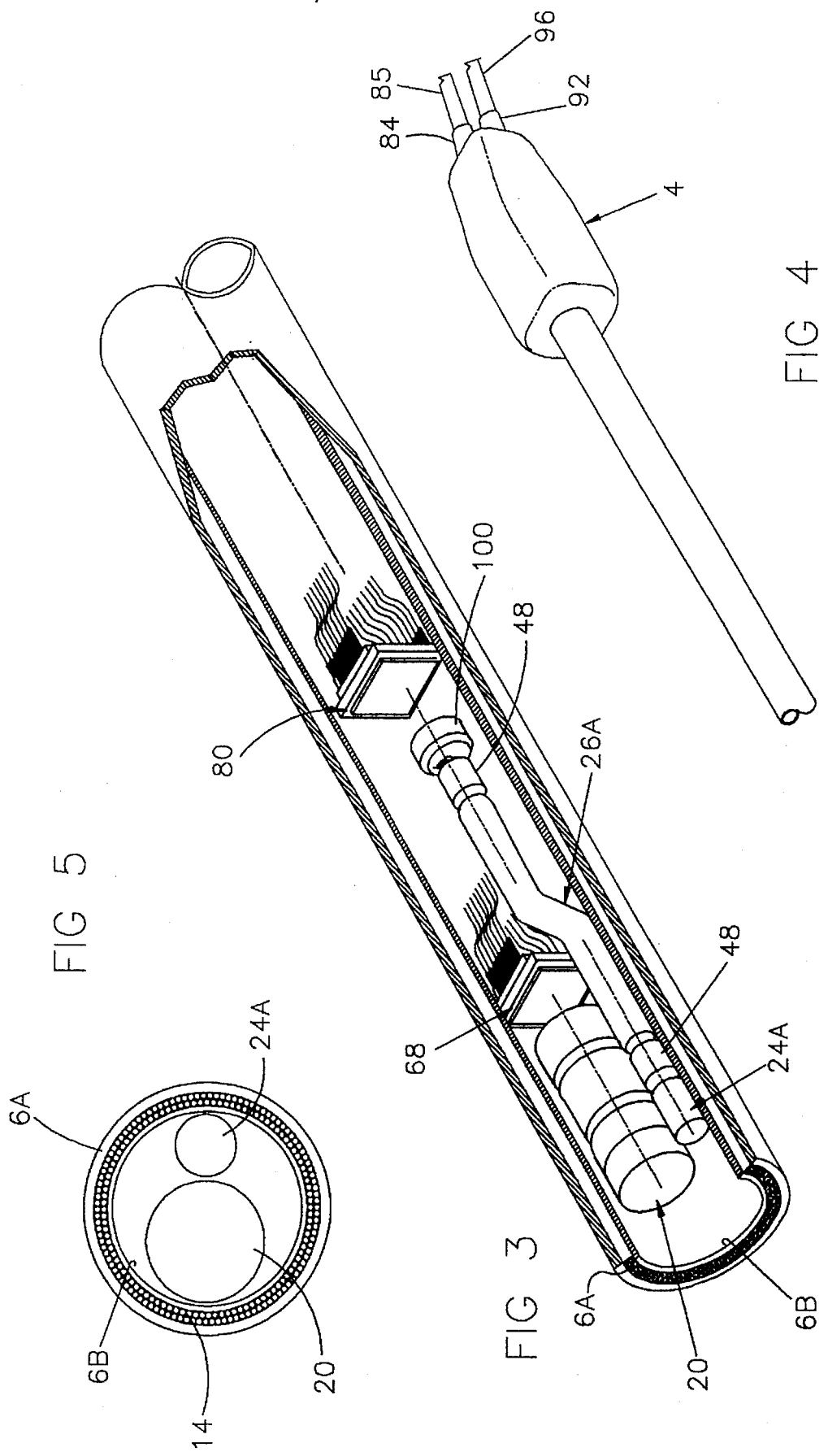

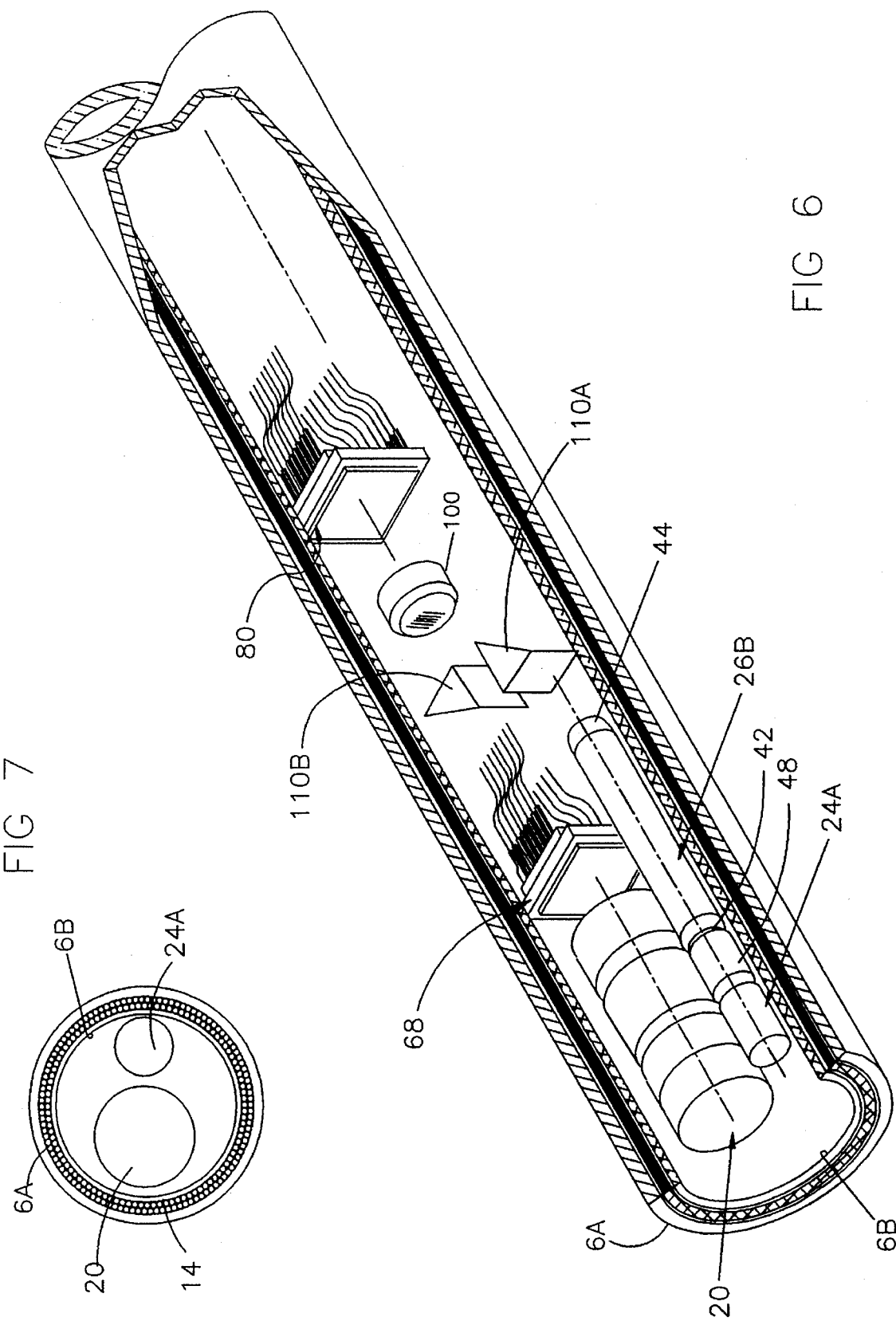

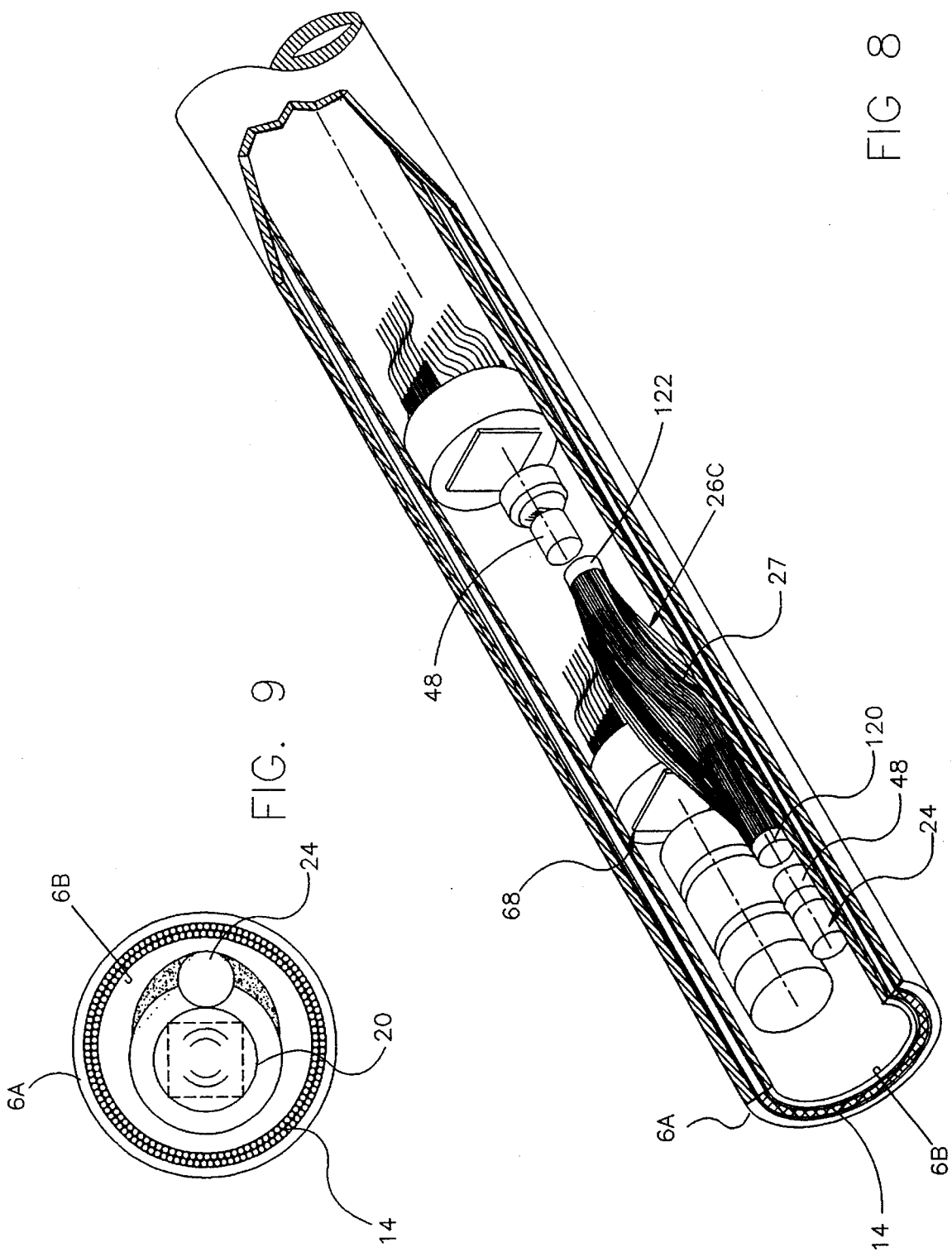

ASYMMETRIC STEREO-OPTIC ENDOSCOPE

FIELD OF THE INVENTION

This invention is a continuation-in-part of U.S. application Ser. No. 08/400,503, filed 7 Mar. 1995 by Koichiro Hori, which in turn is a continuation of U.S. application Ser. No. 07/967,996, filed by Koichiro Hori on 28 Oct., 1992 for "Electronic Endoscope", now abandoned.

This invention relates generally to endoscopes and more particularly to stereo endoscopes that utilize asymmetric optics to provide high quality optical clarity and depth perception.

BACKGROUND OF THE INVENTION

Endoscopes have numerous uses and have proven particularly advantageous in minimally invasive surgery. By inserting an endoscope into a human body through a natural body opening or via a small surgical incision (or via a cannula inserted through the incised tissue), organs, joints, internal body cavities, and other body parts may be observed close up without the need for making large surgical openings. Typically, an endoscope is constructed with an elongate insertion portion having an optical system that comprises an optical objective lens unit adjacent the distal (front) end of the insertion portion, and an image relaying means behind and in alignment with the objective lens unit, and either an optical or electronic imaging means posterior to the image relaying means for providing a display of the viewed image. In electronic endoscopes, i.e., endoscopes using electronic rather than optical imaging means, the imaging means commonly comprises a solid state video sensor located in the insertion portion or adjacent to the proximal (rear) end of the insertion portion, with the sensor providing output signals that are used to generate a video signal input for driving a video monitor video monitor which is adapted to display the viewed image represented by the output signals of the video sensor.

Conventional monocular optical system endoscopes are limited to providing two dimensional images that lack any perspective of depth. Thus, although details of the viewed object may be quite clear in the horizontal and vertical directions, the lack of depth perception often brings confusion when the position of the viewed object is being judged relative to that of another object.

Stereo endoscopes eliminate or substantially reduce the depth visualization problem encountered with monocular optical system endoscopes. Conventional stereo endoscopes comprise two identical objective optical lens systems that are located side-by-side at the distal end of the insertion portion and are disposed so as to obtain the parallax required to realize a stereoscopic view, i.e., so as to capture two offset images of the same object from different angles. The two offset images are transmitted by separate image-relaying means to separate imaging means. The imaging means may be purely optical, comprising a binocular optical viewing assembly whereby the viewing person realizes a stereoscopic view of the viewed object from the two offset images. That kind of imaging arrangement is shown by U.S. Pat. No. 3,655,259 (see also FIG. 3 of U.S. Pat. No. 4,862,873). Alternatively the imaging means may comprise a pair of video sensors, with the output of the sensors being used to drive an external video monitor. The latter's input circuits are connected by video processing and control circuits to the two video sensors, whereby the stereo image pair represented by the output signals of the two video sensors cause the monitor to generate a stereo image display having the parallax of the two offset images. Observing and appreciating the stereoscopic image display provided by the monitor requires the use of specially designed 3D eyeglasses and involves an after-image phenomenon, as disclosed by U.S. Pat. No. 4,862,873. As a further alternative, the external video monitor may be replaced by a 3D headset in the form of spectacles that incorporate two separate video display means, one for each eye.

Unfortunately the advancement from single channel endoscopes to stereo endoscopes is complicated by the need to accommodate two like optical channels, since having two side-by-side optical channels appears to require, an increase in the outer diameter ("o.d.") of the insertion portion of the endoscope. The o.d. size problem is further complicated if the stereo endoscope is to incorporate two video sensors in its insertion portion, even with the smallest video sensors currently available. Of course, achieving stereoscopic capability by using two substantially identical optical channels offers the advantage that since the two systems are identical, their images are optically symmetrical. As used herein, the term "optically symmetrical" is intended to denote that the two systems are identical in magnification (power), orientation, the field of view (i.e., the angle encompassed by the objective lens unit), focus and optical clarity.

However, the need to maintain optical symmetry in a stereo endoscope tends to increase manufacturing cost, thereby discouraging purchase and use of stereo endoscopes. In addition, surgeons practicing minimally invasive surgery favor endoscopes with an insertion portion having a maximum outside diameter ("o.d.") of about 10 mm or smaller. Insertion portions with a larger o.d. may not be feasible or welcome for specific endoscope applications for various reasons, e.g., because of the nature of the surgical site, lack of compatibility with other instruments such as cannulas, or for cosmetic reasons or for reason of patient well-being.

The requirement of an endoscope o.d. of approximately 10 mm is easily satisfied in the case of conventional single channel endoscopes. In such case the objective lens unit or system may occupy a substantial portion of the cross-sectional area of the endoscope tube (i.e., the insertion portion). Thus, for example, the objective lens unit may have an o.d. as large as 7–8 mm in an endoscope tube having a 10 mm o.d. and a wall thickness of about 1–2 mm.

It is difficult to keep the o.d. of the insertion portion of the endoscope to about 10 mm if two objective lenses are disposed side-by-side without sacrificing image quality. Of course, the diameters of the two objective lens systems may be decreased so as to respect the 10 mm o.d. limitation, but reducing the diameters of the objective lens systems introduces other complications such as reducing image brightness and otherwise detracting from the quality of the image seen by the user.

U.S. Pat. No. 5,166,787 attempts to solve some of the design problems associated with electronic endoscopes by providing the insertion portion with two video units (each comprising an objective lens and an image sensor or recorder) that are disposed one behind the other when the endoscope is inserted into a cavity to be examined and are deployed by swinging outwardly into side-by-side relation after insertion into the cavity. However, the form of endoscope structure disclosed by U.S. Pat. No. 5,166,787 is relatively complicated and expensive to make, and its use is affected by the need to (a) deploy the video units into side-by-side position in order to make the needed observations in the body cavity and (b) move them into a tandem relationship in order to permit insertion and withdrawal of the endoscope. Moreover, the fact that at least one video unit is movable into and out of a nesting position within the endoscope housing tends to complicate provision of means for transmitting adequate light to the forward end of the endoscope. Also, as the insertion portion of the endoscope is maneuvered for viewing purposes, the movable video unit may engage an obstruction such as tissue or an organ that offers enough resistance to impede angular shifting movement of one movable video unit relative to the other unit, thereby hampering deployment into the position required to produce an acceptable stereoscopic display of the viewed surgical site.

OBJECTS AND SUMMARY OF THE INVENTION

Accordingly the primary object of the present invention is to provide new and improved electronic stereo endoscopes.

A more specific object of the present invention is to provide an improved stereo endoscope of the type comprising first and second parallel objective lens systems for generating left and right optical images respectively of a viewed object or target, and first and second miniature solid state optical sensing means (video sensors) for receiving said left and right images respectively and generating in response to said images left and right electrical signals representative of said left and right optical images, with those electrical signals being used to generate video images corresponding to the viewed optical images.

A further object of the present invention is to provide a stereo endoscope apparatus for use in minimally invasive surgery which is characterized by a novel combination of optical systems and video sensors that provide stereoscopic capability while allowing the diameter of the endoscope's insertion portion to be kept within a predetermined maximum limit.

Another object is to provide a dual optical channel endoscope with a predetermined o.d. that is capable of providing a stereo image having substantially the brightness and quality of a 2-dimensional image produced by a single optical channel endoscope with the same o.d.

Still another object is to provide a stereo endoscope having an insertion portion in the form of a tube that contain two optical channels and means for transmitting light to the surgical site immediately in front of the insertion portion.

A further object is to provide a stereoscopic electronic endoscope that is based on the process of interocular suppression referred to hereinafter.

These and other objects of the present invention hereinafter described or rendered obvious are achieved by providing an electronic stereo endoscope having a tubular insertion portion characterized by a pair of adjacent asymmetric optical systems that comprise parts of a primary imaging channel and a secondary imaging channel. Associated with each channel is a solid state electronic imaging means positioned to receive the images relayed by the primary and secondary image-relaying means. These imaging means provide output signals that are used to generate video displays of a viewed target. According to this invention, the optical portion of the primary channel comprises a relatively large objective lens system and a primary optical image-relaying means designed to provide sharply focussed first images of a viewed target that are substantially free of aberrations. Also according to this invention, the optical portion of the secondary channel comprises a relatively small diameter objective lens system and a secondary image-relaying means designed to provide second images of the viewed target, the secondary channel being designed to satisfy the criterion of relaying enough light and image information to provide an acceptable stereoscopic capability.

The optical components (lenses) used in the primary channel are of high quality, free of aberrations and designed to generate and relay sharply focussed images. The components of the secondary channel may be of the same quality as the optical elements of the primary channel, so as to provide images that are comparable in most respects to those provided by the primary channel, subject to the limitations on image quality caused by the smaller aperture and gross light transmission capability of the optics of the secondary channel. Preferably, for commercial advantage purposes only, the secondary channel optical system is made of components that are less expensive than those used for the primary channel, even though that arrangement results in the secondary channel providing images that are of lesser quality than the images passed by the primary channel. By way of example, the optical elements of the secondary channel may be made of a low cost glass or a transparent plastic such as a polycarbonate or a polyacrylate.

It has been discovered that the arrangement of a larger o.d., higher optical quality primary channel objective system adjacent to a smaller o.d., lesser optical quality secondary channel objective system is not only capable of providing a pair of offset images that can be combined to provide a stereoscopic image, but in addition that stereo image is perceived by the viewer as being substantially or nearly the same as that achieved with a dual channel stereo endoscope having two identical objective lens systems of the same size, power and quality as the aforementioned relatively large o.d. primary channel objective lens system.

The foregoing asymmetric arrangement leads to ocular dominance of the images provided by the primary imaging channel and interocular suppression of the images from the secondary imaging channel. In other words, when an object or target is being viewed via the primary and secondary channels, the limited quality (and/or unclear or less clear) image received from the secondary channel will be suppressed by the viewer as a consequence of sensing a larger, better focused and detailed image from the primary channel. As a result, the viewer will see a stereoscopic image, but the stereo image will be characterized by the sharp focus, high definition and resolution, and greater brightness of the image communicated by the primary channel. More specifically, the image from the primary channel provides detailed ocular information while the image from the secondary channel only needs to transmit ocular information sufficient to provide a perception Of depth to the image seen by the observer. Of course, as noted above, the secondary channel may be designed and adapted to provide a high quality in-focus image, but it still will involve a smaller diameter objective lens and image-relaying means in order to maintain the outside diameter of the insertion portion within predetermined limits, e.g., about 10 mm. for endoscopes designed for minimally invasive surgery. It is to be appreciated that even though the optical system of the secondary channel is made up of lenses comparable in quality to those of the primary channel, the image passed by that channel will be of lesser brightness than the image passed by the primary channel, and the image passed by the primary channel will still dominate the image passed by the secondary channel, so that the viewer will not tend to notice that the two channels are asymmetric in brightness.

The foregoing objects as well as other specific features of the invention are disclosed or rendered obvious by the following detailed description when read in conjunction with the accompanying drawings.

BRIEF DESCRIPTION OF THE DRAWINGS

FIG. 3 is a fragmentary perspective view, partly in section and on an enlarged scale, of the insertion portion of a second and preferred embodiment of the invention;

FIG. 4 is a fragmentary perspective view showing that the insertion portion of FIG. 3 is attached to a handle assembly;

FIG. 5 is a front end view of the endoscope shown in FIGS. 3 and 4;

FIG. 6 is a view like FIG. 3 of the insertion portion of a third embodiment of the present invention;

FIG. 7 is a front end view of the endoscope insertion portion shown in FIG. 6;

FIG. 8 is a fragmentary perspective view like FIGS. 3 and 6, of the insertion portion of a fourth embodiment of the invention and FIG. 9 is a front end view of the insertion portion shown in FIG. 8.

In the several figures, like components are designated by like numerals. Also, the spacing between certain components is exaggerated for convenience of illustration and to facilitate understanding the invention.

DETAILED DESCRIPTION OF THE PREFERRED EMBODIMENT

Figure 1:
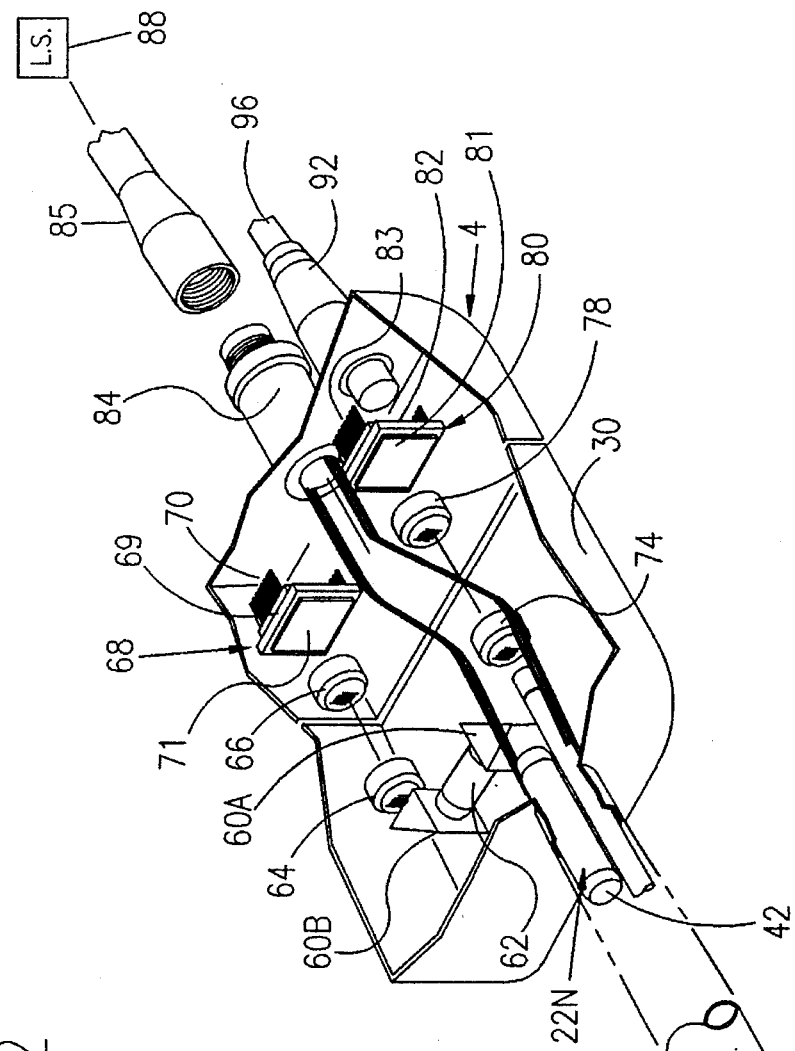
FIG. 1 is a fragmentary perspective view of an asymmetric stereo endoscope constituting a first embodiment of the present invention.
Figure 2:
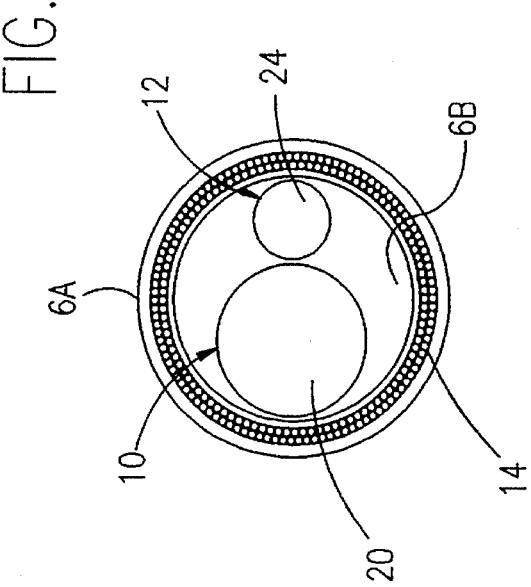
FIG. 2 is a front end view of the same endoscope.

FIGS. 1 and 2 illustrate a first embodiment of the present invention. In FIG. 1, there is shown an optically asymmetric electronic stereo endoscope comprising an elongated tubular insertion portion 2 connected to and supported by a box-like handle assembly 4. The insertion portion 2 comprises a dual tube assembly in the form of two concentric mutually-spaced cylindrical tubes 6A and 6B (hereinafter collectively identified as the "endoscope tube"). Tubes 6A and 6B are fabricated from a suitably rigid material, e.g., a metal such as stainless steel or a plastic or composite material, so as to facilitate maneuvering of the insertion portion through a surgical incision into a desired viewing position. Preferably tubes 6A and 6B are cylindrical as shown in FIG. 2, although they may be formed with some other cross-sectional shape, e.g., an elliptical shape. As seen best in FIG. 2, the annular space between tubes 6A and 6B houses an array of optical fibers 14 that serve as means for illuminating the area immediately in front of the front (distal) end the dual tube assembly. The rear ends of fibers 14 are connected to a light source whereby to achieve the objective of having light pass out of the front end of the fibers to illuminate the surgical site viewed with the endoscope.

The endoscope tube houses a primary imaging channel and a secondary imaging channel identified generally by numerals 10 and 12 respectively. Primary channel 10 and secondary channel 12 provide separate pathways through which images are generated and relayed. For convenience, the primary and secondary optical channels and their corresponding imaging means may be referred to by the designations "right" and "left" respectively, to indicate their respective positions relative to the left and right eyes of an observer of the viewed target. In accordance with this invention, the images relayed by primary channel 10 and secondary channel 12 need not be symmetrical to preserve stereo imaging capability. Only one channel needs to provide an image that has high resolution and is in sharp focus in order to get satisfactory stereo imaging, i.e., stereo imaging characterized by high resolution of details.

The invention requires that the two channels have the same field of view (preferably but not necessarily a field of view of about 70 degrees for most endoscopes), equal geometric distortion (if any), and equal power. Preferably the primary channel uses a multiple glass lens objective that is designed to provide high quality color and image resolution and overcome likely aberrations. Also the primary channel is designed to provide sharp focussing of the primary image on the solid state imaging means.

While the secondary channel may also use a multiple glass lens objective, it is not necessary to do so, since high quality resolution and color and absence of aberrations are not requirements of the secondary channel. Apart from having the same field of view and substantially the same geometric distortion characteristics of the primary channel, the minimum requirement of the secondary channel is that it provide a reasonably focussed image, i.e., an image focus that is close to that of the primary channel. What is a reasonably focussed image will vary as a function of the quality of the image provided by the primary channel, with the acceptable differential in image sharpness varying inversely with the quality of the image provided by the primary channel. In other words, the sharper the primary channel image, the less sharp need be the focussing characteristic of the secondary channel. The essential thing is that the viewer be provided with enough information via the two channels to perceive a focussed stereo image.

The feasibility of the concept of providing a stereo endoscope where only one of its two channels is required to provide a sharply focussed image is related to a process described by C. Schor, and L. Landsman, *Ocular Dominance and the Interocular Suppression of Blur in Monovision*, Am. J. Optom & Physical Optics 1987; 64(10): 723–730. The information contained in that technical article that is relevant to the present invention is incorporated herein by reference. The process known as interocular suppression described by Schor et al generally occurs when there is an image clarity difference between two eyes. Thus, when blurred portions of an image perceived within the retina of one eye are accompanied by a sharply focused image within the retina of the second eye, the brain naturally suppresses the blurred portions of the image seen by the one eye in preference to the sharply focussed high resolution image see by the second eye, so that what the viewer sees is a substantially clear and focussed image based primarily on the information received by the second eye but characterized by the perception of depth supplied by the other eye, i.e., a stereo image.

Accordingly in the embodiment of the invention shown in FIGS. 1 and 2, primary channel 10 comprises an image-forming optical system characterized by a relatively large diameter objective lens system or unit 20 and a primary image relaying means 22 (a–n) hereinafter described. The secondary channel 12 comprises an image-forming optical system characterized by a relatively small diameter objective lens system or unit 24 and a secondary image relaying means 26 hereinafter described.

The relatively large objective system or unit 20 of primary channel 10 may comprise a single high quality lens, but preferably it comprises two or more high quality lenses designed to provide a suitable field of view and to acquire and transmit a clear, highly focussed and detailed image of an object or target in its field of view. On the other hand, since a high resolution image may but need not be provided by secondary channel 12, it is preferred that the small diameter objective lens system 24 be of limited quality and hence less expensive, e.g., made of a gradient index glass or a transparent plastic such as polycarbonate or a polyacrylane. Like lens system 20, the smaller diameter objective lens system 24 may comprise a single lens or two or more lenses designed and arranged to provide a suitable field of view. By way of example, lens systems 20 and 24 may be designed and mounted like or similar to the objective systems disclosed by U.S. Pat. Nos. 4,491,865, 4,832,003, and 4,867,137. Still other suitable objective system designs known to persons skilled in the art may be used in practicing this invention.

Lens system 24 has a field of view substantially equal to that of objective lens system 20. The field of view may be determined according to the intended use of the endoscope. By way of example but not limitation, for an endoscope designed for laparoscopic surgery, each objective lens unit may be designed to provide a field of view in the range of 65 to 80 degrees. The convergence point of the two objective lenses may vary according to design requirements, e.g. their fields of view may converge about 3.0 cm in front of the distal (front) end of the endoscope tube for some surgical applications.

Preferably, but not necessarily, lens system 20 comprises two or more high quality glass lenses, each having a uniform index of refraction, with the lenses being designed to provide a sharply focussed image that is substantially free of any aberrations such as chromatic aberrations. The secondary objective system 24 may comprise one or more glass lenses equal in quality to lens system 20. Preferably and by way of example, the secondary objective system 24 may comprise one or more lenses having a non-uniform or gradient refractive index and/or chromatic or other aberrations, with the lenses being designed with the intention of providing a sharply focussed image for relaying to the imaging means. Unfortunately the ability to obtain a sharply focussed images is limited by the gradient refractive index and the inherent aberrations of the secondary objective system. Nevertheless, using such limited quality lenses offers the advantages of lower cost and the ability to capture enough light and information to preserve three dimensional imaging.

The two objective lens systems 20 and 24 are situated at the distal (front) end of the dual tube assembly 6A, 6b and are locked thereto by suitable means, e.g., by a potting compound (not shown) or a friction fit in tube 6B. For an endoscope designed for laparoscopic surgery, it is preferred that tube 6A have an outer diameter (o.d.) of 10.0 mm and tube 6B have an inner diameter (i.d.) of 9.5–9.7 mm. The annular space between the two tubes is just large enough to accommodate one or two layers of optical fibers 14. Also in such case, objective lens unit 20 has an o.d. of about 5.0 to 6.0 mm and objective lens unit 24 has an o.d. of about 2.0 mm, with the two objective lens units contacting one another as shown in FIG. 2, so as to provide a center axis-to-axis spacing of about 3.5 to 4.0 mm. By virtue of being adjacent to one another, objectives 20 and 24 provide images from offsetting angles, which in turn are used to convey a sense of depth perception as is required to provide a three-dimensional observation or image.

Preferably but not necessarily, objective units 20 and 24 comprise cylindrical mounting rings or housings (not shown) that surround and support the several lenses that form the objective units. Those mounting rings or housings are made relatively thin, so as to maximize the diameters of the lenses and so that the diameter of the effective aperture of each objective system is almost the same as the o.d. of the lenses that make up the system.

The primary image relaying means 22, located behind and adjacent to lens system 20, comprises an end-to-end array of a plurality of rod-like relay lens assemblies 22a–n (where "n" is the last lens) which preferably are made in accordance with the teachings of U.S. Pat. No. 3,257,902, issued 25 Jun. 1966 to Harold H. Hopkins for "Optical System Having Rod-Like Lenses". Use of rod-type lenses in endoscopes is shown by the Hopkins patent (supra) and also by U.S. Pat. No. 3,655,259. Further details of the primary image relaying lenses are set forth hereinafter. Each of the relay lens assemblies 22a–n that make up image-relaying means 22 preferably has an outside diameter substantially identical to that of lens unit 20.

Each of the relay lens assemblies 22a–n is an assembly of a cylindrical rod-like plano-plano lens 40 and correcting convex lenses 42 and 44 attached to the opposite ends of each lens 40. Lenses 42 and 44 are designed to assure optimum image transmission. In accordance with accepted practices, the outer circumferential surfaces of lenses 40, 42 and 44 are coated with a non-reflecting material (not shown). The several relay lens assemblies 22a–n are positioned in tube 6B so that the correcting lens 42 for one lens 40 is spaced a precise distance from the correcting lens 44 of the preceding lens 40. Also the first-in-line or forward-most one of the relay lens assemblies has its correcting lens 42 spaced a precise distance from objective lens unit 20. As shown in FIG. 1, spacing of the several relay lens assemblies is achieved by cylindrical spacing rings 48 having internal shoulders (not shown) that are engaged and supported by correcting lenses 42 and 44 of the adjacent relay lens assemblies. The rings 48 facilitate insertion and positioning of the relay lens assemblies in tube 6B. The relay lens assemblies 22a–n are spaced so as to assure that the image transmitted from the lens 44 of one relay lens assembly is properly focussed on the lens 42 of the next adjacent relay lens assembly.

The secondary image relaying means 26 also may consist of a plurality of rod-like lenses similar to those described in said U.S. Pat. No. 3,257,902, but preferably for reason of reduced cost it consists of only a single gradient index rod-type relay lens that is long enough to extend into handle assembly 4.

The secondary image-relaying means 26 also preferably has an opaque or non-reflecting coating (not shown) on its circumferential surface. The optical quality of the secondary relay means may be as good as that of the primary relay means, but for reasons of reducing cost the secondary relay means may be formed of inferior and less expensive lenses.

Primary image relaying means 22 and secondary image relaying means 26 extend for the full length of the endoscope tube 6A, 6B into handle assembly 4. The latter comprises a box-like housing 30 to which tube 6A, 6B is attached by various conventional methods or means, for example, a press-fit, brazing, welding, or a threaded coupling.

In the embodiment of FIG. 1, housing 30 houses electronic right and left imaging means. As used herein with respect to the imaging means, the terms "right" and "left" are intended to denote the imaging means corresponding to the observers right and left eyes respectively. In this particular embodiment of the invention, the right imaging means receives optical information from primary channel 10 and the left imaging means receives optical information from secondary channel 12. The primary channel further comprises in sequence, a pair of optical prisms 60A, 60B, a rod-type relay lens 62, an ocular lens 64, and a focusing lens 66 for transmitting images from the rearmost relay lens 22n to a right imaging means in the form of a video unit 68 that comprises a semiconductor image sensor 69, i.e., a photodetector, such as a charged coupled device (CCD), and terminal means 70 on the sensor for connecting the output of that sensor to a control system (not shown). Preferably, but not necessarily, image sensor 69 has a transparent protective cover 71 overlying its front image-receiving surface. Prisms 60A, 60B and rod lens 62 are designed to relay clear and detailed images to video unit 68.

The secondary channel comprises an ocular lens 74 and a focussing lens 78 for relaying images from relay lens 26 to a left imaging means in the form of a video unit 80 that is like video unit 68 and is disposed in axial alignment with the secondary image relaying means 26. Video unit 80 comprises a CCD image sensor 82 having terminal means 83 for connecting its output signals to the aforementioned control system (not shown). Sensor 80 also preferably has a transparent protective cover 81 overlying its front image-receiving surface.

The rear ends of optical fibers 14 are gathered together inside of housing 30 and attached to a light cable connector assembly 84 attached to the rear end wall of the handle housing. Connector assembly is connected to a fiber optic cable 85 that is used to couple optical fibers 14 to a suitable remote light source "L.S." represented schematically at 88. The terminals of the two CCD video units 68 and 80 are connected by suitable harnesses (not shown) to an electrical connector assembly 92 that is mounted on the rear end wall of housing 30 and is releasably connected to an electrical cable 96 that leads to an electrical control system (not shown) that is adapted to process the video signals from sensors 68 and 80 and apply them to a TV monitor (not shown) where the two images are displayed for viewing as a stereo image.

FIGS. 3–5 show an alternative and preferred embodiment of the invention. In this embodiment, the insertion portion comprises the dual tube assembly consisting of concentric tubes 6A and 6B and light fibers 14 previously described. The primary optical channel consists of the relatively large diameter objective lens system or unit 20 and video unit 68, both inside of and fixed relative to tube 6B. The secondary channel comprises a relatively small diameter secondary objective lens system 24A and a secondary relay lens system 26A, also both disposed within and fixed against movement relative to inner tube 6B. The secondary objective lens 24A is a gradient index lens. As with the embodiment of FIGS. 1 and 2, the secondary optical relay means 26A has an o.d. substantially identical to that of secondary objective lens unit 24, so as to assure that it will adequately relay the optical information passed by objective lens system 24. However, in this case, the secondary optical relay lens system 26A is an optical conduit made up of a coherent bundle of optical fibers that are fused together. The opposite end surfaces of the conduit are polished flat and smooth. The conduit may be flexible; however, as a practical matter it tends to be stiff and hence it is preformed with an offset as shown, so as to allow its front end to be axially aligned with secondary objective lens 24A and its rear end to be axially aligned with a focussing lens 100 that is located in front of and aligned with video unit 80. The latter is located behind video unit 68 inside of tube 6B, and is locked against movement relative to that tube and objective lens unit 20.

The front end of secondary optical relay lens system 26A is mechanically and optically coupled to the secondary objective 24A by a spacer ring 48. The rear (proximal) end of the secondary optical relay system 26A is coupled to focussing lens 100 by another spacer ring 48. Lens 100 is fixed against movement relative to inner tube 6B and video unit 80.

Still referring to FIGS. 3–5, as with the embodiment of FIGS. 1 and 2, the tube assembly 6A,6B extends into and is supported by a handle assembly 4. The latter is provided with a pair of connectors 84 and 92 that serve to accommodate a fiber optic cable 85 and an electrical cable 96. The opposite ends (not shown) of cables 85 and 96 are adapted to be connected respectively to a light source (not shown) and a video control and display system (also not shown) as previously described.

The instrument disclosed in FIGS. 3–5 offers the same advantages of the embodiment of FIGS. 1 and 2, and also the further advantage that it is more simple in the sense that a number of components are omitted. By mounting the two video units 68 and 80 within the dual tube assembly 6A,6B, an advantage is obtained in that the handle assembly may be made smaller and also will be less expensive because of the omission of the optical elements shown in FIG. 1. Additionally, if desired, the electrically-powered light source used to illuminate the fibers 14 may be embodied in the handle assembly, with the result only a single electrical cable need be used, albeit that the electrical cable assembly must include wire leads for the two video units 68 and 80 and also wire leads for providing electrical power to the light source. A more important advantage is that the two video units are disposed in tandem, thus reducing the allowable o.d. of the insertion portion.

FIGS. 6 and 7 show a third embodiment of the invention. As with the instrument system of FIGS. 3–5, the endoscope of FIGS. 6 and 7 embodies two video units 68 and 80 within the dual tube assembly 6A,6B. In addition, the embodiment of FIGS. 6 and 7 is essentially the same as that of FIGS. 3–5, with the exception that the offset-contoured coherent fused fiber conduit 26A of FIG. 3 is replaced with a straight optical rod relay lens 26B made in accordance with the teachings of Hopkins U.S. Pat. No. 3,257,902. Relay lens 26B has convex correcting lenses 42 and 44 at its opposite ends and a spacer ring 48 couples gradient lens objective unit 24A to relay lens 26B. Whereas the fiber bundle 26A in FIG. 3 was bent so as to allow the two video units to be mounted directly behind one another, in this case the same result is achieved by utilizing a pair of prisms 110A and 110B with prism 110A being located directly in line with the relay lens 26B and the prism 110B being mounted in line with focussing lens 100, so that the image,passed by the prisms will be substantially centered on the axis of lens 100. The latter is fixed directly in front of video unit 80. With this arrangement, the two video units may be mounted directly behind one another in line with the primary objective 20.

Although not shown in FIG. 6, it should be understood that the endoscope tube 6A, 6B is attached to a handle assembly like that shown in FIG. 4, with light fibers 14 and sensors 68 and 80 being coupled to connectors 84 and 92 for connection to an external light source and also an electronic video control and display system (both not shown) in the same manner as the corresponding elements of the embodiments of FIGS. 1–5.

FIGS. 8 and 9 illustrate another asymmetrical electronic endoscope made according to the present invention. This embodiment is similar to that of FIG. 3. However, in this case the image-relaying means 26C of the secondary channel consists of a coherent bundle of non-fused optical fibers 27 with the fibers being loose relative to one another except at their opposite ends where they are captured in suitable ring-like guides 120 and 122 that mate with and are supported by spacers 48 that are fixed in tubed 6B. For convenience, the ends of the fibers 27 are shown spaced from spacers 48 for the purpose of illustrating the guides 120 and 122. The latter are sized to nest inside of the adjacent spacers 48. The loose intermediate portions of fibers 27 are contoured around the forward video unit 68. This optical fiber arrangement offers the advantage that the optical fibers can be positioned so that they will not interfere with positioning or operation of the front CCD video unit 68, and offers the further advantage of avoiding use of a contoured fused optical fiber conduit as required by the embodiment of FIG. 3.

It is to be noted that the video units need not have a square configuration as shown in FIGS. 1 and 3, but instead may have a different shape, e.g., a circular shape as shown at 130 in FIG. 8.

Exact details of imaging devices 68 and 80 are not provided herein since their form is not critical to the invention and instead those devices may take various forms, e.g., it may be like the ones described and illustrated in U.S. Pat. Nos. 4,448,039; 4,491,865; 4,867,137; and 5,166,787 and may comprise a CCD chip as shown in U.S. Pat. Nos. 4,745,470; 4,745,471; and 5,021,888. Such solid state CCD devices have a lead frame or chip carrier with terminal pins adapted to mate with a conventional connector on the end of a multi-strand wire harness that is used to couple the imaging device to external electronic video circuits.

It is believed to be obvious from the foregoing description that the invention offers the advantage of providing a stereoscopic endoscope that is characterized by an insertion portion with a minimal outside diameter, while at the same time offering the further advantage of a high quality stereoscopic image. In all of the embodiments described above, the secondary optical channel provides enough optical information to establish a stereoscopic image, while the primary optical channel provides all of the details which the user desires to observe.

A further advantage of the invention is that the arrangement of its components does not limit the form or capability of whatever control and display system is provided for processing and transmitting the outputs from the two video imaging devices and providing a visual display in response to those video outputs. Thus, for example, the control and display system may incorporate digital processing for parallax correction, i.e., left and right channel alignment. Still other manipulation techniques of the signals produced by the video sensors may be used to enhance the viewer's perception of depth and color in the viewed stereo image produced from combining the offset images produced by the two video sensors.

The control and video processing circuits used to interface the video units 68 and 80 with the display monitor, and also the monitor or other display device used to display the viewed stereo images, may take various forms and may be similar, for example, to the circuits shown in U.S. Pat. Nos. 4,873,572 and 4,862,873. To the extent necessary, the disclosures of these patents are incorporated herein by reference thereto.

It is to be recognized that although the foregoing invention was developed for the purpose of minimizing the outside diameter of the insertion portion of the endoscope, the invention is not limited to endoscopes for minimally invasive surgery; to the contrary the same organization of components may be used in larger endoscopes and also for other stereo telescopic type devices, including boroscopes.

The invention is susceptible of various modifications. For one thing, the video unit need not be limited to a CCD (charge coupled device) since CCD devices are only one type of solid state image sensors. For example, the invention may utilize solid state image sensors of the type known as CID (charge injection device) and CPD (charge prime device). The video units preferably are selected so as to be able to provide adequate color rendition in the displayed image seen by the viewer. Similarly, each objective lens system may comprise one or more lenses, e.g. full doublets. Also the optical components of the objective lens systems and the image-relaying lens systems of the two channels may be made of various glasses or a suitable synthetic substitute, e.g. a polycarbonate or an acrylate polymer. The design of optical components is accomplished with a concern for maximizing color rendition and balance in the display of images. It also is to be understood that some or all of the optical components may be made with a gradient index of refraction. Similarly, the gradient index objective lens unit 24A used in the embodiments of FIGS. 3 and 6 could be replaced by non-gradient index lenses. Also, although it is preferred to use less expensive optical components for the secondary channel, the invention may be practiced by making the optical components of the secondary channel of the same quality material and workmanship as those used in the primary channel, so that the only difference between the images provided by the two channels are those attributable solely to the difference between the o.d. of the primary objective lens system and the o.d. of the secondary objective lens system.

Other advantages and modifications of the invention are believed to be obvious to persons skilled in the art.

What is claimed is:

1. A stereo endoscope comprising:

first and second solid state image sensors;

an elongate tube having a front end and a rear end;

first and second discrete optical channels and light transmitting means disposed within said tube;

said first optical channel comprising a first objective lens system disposed adjacent the front end of said tube and first image-relaying means for receiving the image presented by said first objective lens system and transmitting same to said first image sensor;

said second optical channel comprising a second objective lens system disposed adjacent the front end of said tube and second image-relaying means for receiving the image presented by said second objective lens system and transmitting same to said second image sensor;

said second objective lens system having a smaller diameter than said first objective lens system.

2. An endoscope according to claim 1 wherein said first and second objective lens systems have the same field of view.

3. An endoscope according to claim 1 wherein said second image-relaying means has a smaller diameter than said first image-relaying means.

4. An endoscope according to claim 1 wherein said first and second imaging means are located inside of said tube.

5. An endoscope according to claim 1 wherein said first and second image sensors are located outside of and behind said tube.

6. An endoscope according to claim 1 wherein said image sensors are located outside of said tube rearwardly of the rear end thereof, and further including optical elements outside of said tube for focussing the image presented by said first and second objective lenses onto said first and second image sensors respectively.

7. An endoscope according to claim 1 wherein said first and second image sensors each comprises a photodetector having an image-receiving surface, and further wherein said first and second image sensors are disposed with their image-receiving surfaces in side-by-side relation with one another.

8. An endoscope according to claim 7 wherein said first and second image sensors are located outside of said tube in a housing attached to said rear end of said tube and, further including at least one optical element for focussing the image relayed by said first image-relaying means onto the image-receiving surface of said first image sensor and at least one optical element for focussing the image relayed by said second image-relaying means onto the image-receiving surface of said second image sensor.

9. An endoscope according to claim 1 wherein said first and second image sensors each comprises a photodetector having an image-receiving surface, and further wherein said first and second image sensors are disposed in tandem with one another inside and lengthwise of said tube.

10. An endoscope according to claim 1 further including a handle attached to the rear end of said tube, and further including electrical connector means carried by said handle for coupling said first and second solid state image sensors to electrical circuits located outside of said handle.

11. An endoscope according to claim 1 wherein said first and second objective lens systems are disposed in a side-by-side relationship, and further wherein said second image sensor is located behind said first image sensor inside of said tube, and said second image-relaying means constitutes an optical fiber bundle extending between said second objective lens and said second image sensor.

12. An endoscope according to claim 11 wherein said optical fiber bundle extends alongside of said first image sensor inside of said tube.

13. An endoscope according to claim 1 wherein said second image sensor is located behind said first image sensor inside of said tube and said second image-relaying means constitutes image-relaying lens means and first and second prisms for relaying the image from said second objective lens to said second image sensor.

14. An endoscope according to claim 13 wherein said second image sensor is located eccentric to the axis of said second objective lens.

15. An endoscope according to claim 13 wherein said second image-relaying lens means comprises a plano-plano optical rod having a first lens mounted at one end for receiving the image projected by said second objective lens and a second lens mounted at its opposite end for transmitting the image from said second objective lens to said first prism, and further wherein said first and second prisms are disposed so as to provide an optical path for the received image that includes a transit portion that extends transversely of said tube.

16. An endoscope according to claim 1 wherein said light transmitting means comprises a plurality of optical fibers disposed between said tube and said first and second objective lenses.

17. An endoscope according to claim 1 further including a second elongate tube surrounding said first-mentioned tube, and further wherein said light transmitting means comprises a plurality of optical fibers disposed between said first-mentioned tube and said second tube.

18. An endoscope according to claim 17 wherein said second tube has a front end that is substantially flush with the front end of said first-mentioned tube, and said plurality of optical fibers have front ends that are substantially flush with the front ends of said tubes.

19. An asymmetric endoscope apparatus for stereo-optically viewing an object comprising:

an insertion portion comprising (a) an elongate tubular member having a front end, a rear end, and an interior surface, (b) a first optical channel comprising a primary objective lens unit and a primary image-relaying means, (c) a second optical channel comprising a secondary objective lens unit and a secondary image-relaying means, said lens units and said image-relaying means being surrounded by said interior surface of said tube, and said primary objective lens unit having a substantially larger diameter than said secondary objective lens unit, and (d) light-conducting means for illuminating the region in front of said front end of said insertion portion, said light-conducting means surrounding said tubular member; and first and second electronic imaging means for receiving the images relayed by said primary and secondary image-relaying means respectively.

20. An endoscope according to claim 19 further including a handle housing attached to said rear end of said elongate tubular member, and means carried by said handle housing for electrically connecting said electronic imaging means to an exterior circuit.

21. An endoscope according to claim 19 wherein said primary image-relaying means of said primary channel comprises a plurality of relay lenses disposed in series along the optical axis of said primary objective lens unit.

22. An endoscope according to claim 19 wherein said first and second imaging means are disposed within said elongate tubular member.

23. An endoscope according to claim 22 wherein said first and second imaging members are solid state photodetectors.

24. An endoscope according to claim 19 wherein said second optical channel comprises a gradient index type objective lens.

25. An endoscope according to claim 19 wherein said secondary image-relaying means comprises a gradient index rod-type lens.

26. An endoscope according to claim 19 wherein said secondary image relaying means comprises a fused image fiber conduit, and said first and second electronic imaging means are disposed in tandem within said tubular member.

27. An endoscope according to claim 19 wherein said secondary image relaying means comprises a coherent bundle of optical fibers, and said first and second electronic imaging means are disposed in tandem within said tubular member.

28. An asymmetric endoscope apparatus for stereo-optically viewing an object comprising:

an elongate tubular insertion portion having an interior surface terminating in an image-receiving end;

a primary optical channel and a secondary optical channel extending side-by-side within and lengthwise of said insertion portion;

said primary optical channel comprising a primary objective lens adjacent the image-receiving end of said insertion portion for forming an image of the viewed object and a primary image-relaying means for relaying said image from said primary objective lens, and said secondary optical channel comprising a secondary objective lens adjacent the said image-receiving end of said insertion portion for forming an image of said viewed object and a secondary image-relaying means for relaying said image from said second objective lens, said secondary objective lens having a smaller diameter than said primary objective lens, and said primary and said secondary image-relaying means being respectively located posterior to said primary and secondary objective lenses;

first and second imaging means for receiving the images of said viewed object relayed by said primary and second image-relaying means respectively; and illuminating means for providing illumination at said image-receiving end of said insertion portion, said illuminating means comprising optical fibers extending lengthwise of said tubular insertion portion.

29. An asymmetric endoscope apparatus according to claim 28 wherein said apparatus further comprises a housing fixedly attached to said insertion portion at an end opposite said image-viewing end.

30. An asymmetric endoscope apparatus according to claim 29 wherein said first and second imaging means are disposed within said housing.

31. An asymmetric endoscope apparatus according to claim 28 wherein said primary image-relaying means comprises a plurality of relay lenses disposed in series lengthwise of said tubular insertion portion.

32. An asymmetric endoscope apparatus according to claim 28 wherein said secondary image-relaying means comprises a plurality of rod-type relay lenses disposed in series with one another lengthwise of said tubular insertion portion.

33. An asymmetric endoscope apparatus as set forth in claim 28 wherein said primary image-relaying means comprises a pair of prisms and a focusing type lens, said pair of prisms being disposed so as to relay said image to said first imaging means so that the path followed by said image to said first imaging means includes a transit that extends at an angle to the axis of said insertion portion.

34. An asymmetric endoscope apparatus according to claim 28 wherein said secondary objective lens or said secondary image relaying means comprises a gradient index type lens.

35. An asymmetric endoscope apparatus according to claim 28 wherein said secondary image-relaying means comprises a fused image fiber conduit.

36. An asymmetric endoscope apparatus according to claim 28 wherein said secondary image-relaying means comprises a coherent bundle of loose fibers.

37. An asymmetric endoscope apparatus according to claim 28 wherein said insertion portion comprises a pair of concentric, mutually-spaced tubes, and said illuminating means comprises optical fibers disposed between and extending lengthwise of said tubes.

38. A stereo endoscope comprising:

an elongate tube having a front end and a rear end;

means for illuminating a target area in front of said front end of said tube;

first and second imaging channels within said tube for capturing first and second offset images respectively of objects in the target area;

each of said channels comprising an optical objective lens system located substantially at said front end of said tube for capturing images of objects in the target area, a solid state imaging means for generating electrical signals in response to images received from said objective lens system with said signals being representative of a video image, and image-relaying means for receiving the image captured by said objective lens system and transmitting the same to said solid state imaging means;

characterized in that the objective lens system of said first channel has a substantially larger diameter than the objective lens system of said second channel.

39. An endoscope according to claim 38 wherein said elongate tube comprises first and second concentric tubular members with said first tubular member surrounding and spaced from said first tubular member, and further wherein said means for illuminating said target area comprises a plurality of light-transmitting fibers located between said first and second tubular members.

40. An endoscope according to claim 38 further including a handle assembly attached to said rear end of said tube, and further including electrical connector means carried by said handle assembly and connected to said solid state imaging means for mating with an exterior cable for transmitting the output signals of said solid state imaging means to a display means that is adapted to produce a stereo display of the offset images captured by said first and second channels.

* * * * *

UNITED STATES PATENT AND TRADEMARK OFFICE
CERTIFICATE OF CORRECTION

PATENT NO. : 5,603,687
DATED : February 18, 1997
INVENTOR(S) : Koichiro Hori et al.

It is certified that error appears in the above-indentified patent and that said Letters Patent is hereby corrected as shown below:

Claim 8, column 13, line 15, insert " , " after the word -- tube --; and

Claim 8, column 13, line 15, delete "and," (second occurrence).

Signed and Sealed this

Twenty-ninth Day of April, 1997

Attest:

BRUCE LEHMAN

Attesting Officer

Commissioner of Patents and Trademarks